(12) United States Patent
Govyadinov et al.

(10) Patent No.: US 10,365,226 B2
(45) Date of Patent: Jul. 30, 2019

(54) MICROFLUIDIC OPTICAL FLUID SENSOR

(71) Applicant: Hewlett-Packard Development Company, L.P., Houston, TX (US)

(72) Inventors: Alexander Govyadinov, Corvallis, OR (US); Charles M. Santori, Palo Alto, CA (US); Anita Rogacs, Palo Alto, CA (US); Diane R. Hammerstad, Corvallis, OR (US); Manish Giri, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 15/546,936

(22) PCT Filed: Apr. 30, 2015

(86) PCT No.: PCT/US2015/028650
§ 371 (c)(1),
(2) Date: Jul. 27, 2017

(87) PCT Pub. No.: WO2016/175862
PCT Pub. Date: Nov. 3, 2016

(65) Prior Publication Data
US 2018/0043687 A1 Feb. 15, 2018

(51) Int. Cl.
*G01N 15/14* (2006.01)
*G01N 21/27* (2006.01)
(Continued)

(52) U.S. Cl.
CPC .............. *G01N 21/85* (2013.01); *G01N 15/14* (2013.01); *G01N 21/27* (2013.01); *G01N 21/64* (2013.01);
(Continued)

(58) Field of Classification Search
CPC .... G01N 15/00; G01N 15/10; G01N 15/1056; G01N 15/14; G01N 15/1404;
(Continued)

(56) References Cited

U.S. PATENT DOCUMENTS 6,100,541 A 8/2000 Nagle et al.
6,438,279 B1 * 8/2002 Craighead .............. G02B 6/136
356/246

(Continued)

FOREIGN PATENT DOCUMENTS

EP       1010975 A1     6/2000
WO    WO-2012131308    10/2012
(Continued)

OTHER PUBLICATIONS

Adams, Mark et al., "Microfluidic integration on detector arrays for absorption and fluorescence micro-spectrometers," 2003, Sensors and Actuators A 104, pp. 25-31.*
(Continued)

*Primary Examiner* — Gordon J Stock, Jr.
(74) *Attorney, Agent, or Firm* — Perry + Currier Inc

(57) ABSTRACT

Provided in one example is an apparatus, including a substrate supporting a microfluidic channel, a bubble jet inertial pump supported by the substrate adjacent the microfluidic channel to pump fluid through the microfluidic channel and an optical sensor on a first side of the microfluidic channel. A light emitter on a second side of the microfluidic channel is to pass light across the microfluidic channel to the optical sensor.

15 Claims, 9 Drawing Sheets

(51) Int. Cl.
| | | |
|---|---|---|
| *G01N 21/64* | (2006.01) | |
| *G01N 21/85* | (2006.01) | |
| *G01V 8/12* | (2006.01) | |
| *B41J 2/125* | (2006.01) | |
| *B41J 2/175* | (2006.01) | |
| *B41J 2/195* | (2006.01) | |

(52) U.S. Cl.
CPC ............... *B41J 2/125* (2013.01); *B41J 2/175* (2013.01); *B41J 2/195* (2013.01); *G01N 2015/149* (2013.01); *G01N 2015/1486* (2013.01); *G01N 2015/1493* (2013.01); *G01N 2021/8557* (2013.01); *G01V 8/12* (2013.01)

(58) Field of Classification Search
CPC .......... G01N 15/1434; G01N 15/1436; G01N 15/1456; G01N 15/1484; G01N 2015/1006; G01N 2015/105; G01N 2015/1081; G01N 2015/1087; G01N 2015/1093; G01N 2015/1477; G01N 2015/1486; G01N 2015/149; G01N 2015/1493; G01N 2015/1497; G01N 21/25; G01N 21/27; G01N 21/31; G01N 21/47; G01N 21/49; G01N 21/53; G01N 21/532; G01N 21/534; G01N 21/55; G01N 21/59; G01N 21/62; G01N 21/63; G01N 21/64; G01N 21/84; G01N 21/85; G01N 2021/8557

See application file for complete search history.

(56) References Cited

U.S. PATENT DOCUMENTS

| | | | | |
|---|---|---|---|---|
| 6,592,733 B1 * | 7/2003 | Foley | ............... | G01N 27/44721 |
| | | | | 204/452 |
| 7,210,937 B1 * | 5/2007 | Raghu | .................... | G09B 23/12 |
| | | | | 434/283 |
| 7,815,871 B2 | 10/2010 | Pamula | | |
| 8,158,082 B2 * | 4/2012 | Imran | .................. | B01J 19/0093 |
| | | | | 422/505 |
| 8,561,456 B2 * | 10/2013 | Meredith | .............. | G01M 3/047 |
| | | | | 356/328 |
| 2004/0005635 A1 | 1/2004 | Goix et al. | | |
| 2004/0161772 A1 * | 8/2004 | Bohm | ....................... | B07C 5/34 |
| | | | | 435/6.16 |
| 2007/0257215 A1 | 11/2007 | Rich | | |
| 2007/0298514 A1 | 12/2007 | Correia et al. | | |
| 2008/0213821 A1 * | 9/2008 | Liu | .................. | B01L 3/502761 |
| | | | | 435/39 |
| 2010/0155572 A1 * | 6/2010 | Kiesel | ....................... | G01J 3/02 |
| | | | | 250/201.1 |
| 2011/0066386 A1 | 3/2011 | Hong et al. | | |
| 2011/0286493 A1 * | 11/2011 | Torniainen | ............. | B41J 2/1404 |
| | | | | 374/33 |
| 2012/0094397 A1 | 4/2012 | Horii | | |
| 2013/0061936 A1 * | 3/2013 | Govyadinov | ........ | B41J 2/14233 |
| | | | | 137/13 |
| 2013/0148113 A1 | 6/2013 | Oku | | |
| 2013/0203157 A1 | 8/2013 | Cheung | | |

FOREIGN PATENT DOCUMENTS

| | | |
|---|---|---|
| WO | WO-2013159189 | 10/2013 |
| WO | WO-2014178827 | 11/2014 |

OTHER PUBLICATIONS

Caputo et al.; Amorphous silicon photosensors integrated in microfluidic structures as a technological demonstrator of a "true" Lab-on-Chip system; Mar. 2015.

Demetri Psaltis, Stephen R. Quake and Changhuei Yang, "Developing optofluidic technology through the fusion of microfluidics and optics," Nature vol. 442, pp. 381-386 (2006) See Fig 2 in particular depicting array of apertures used for high resolution.

Martins et al.; Toward Complete Miniaturisation of Flow Injection Analysis Systems: Microfluidic Enhancement of Chemiluminescent Detection; Oct. 16, 2014.

McGuinness et al., Microfluidic Sensing Device, Appln. No. PCT/US2014/0137848; Filed Jan. 30, 2014.

PCT International Search Report and Written Opinion, Dec. 10, 2015, PCT Application No. PCT/US2015/028650, Korean Intellectual Property Office, 13 pp.

Wang et al.; Integrated Thin-film Polymer/fullerene Photodetectors for On-chip Microfluidic Chemiluminescence Detection; Oct. 17, 2006; http://pubs rsc org/en/content/articlelanding/2007/1c/b611067c/unauth#!divAbstract.

\* cited by examiner

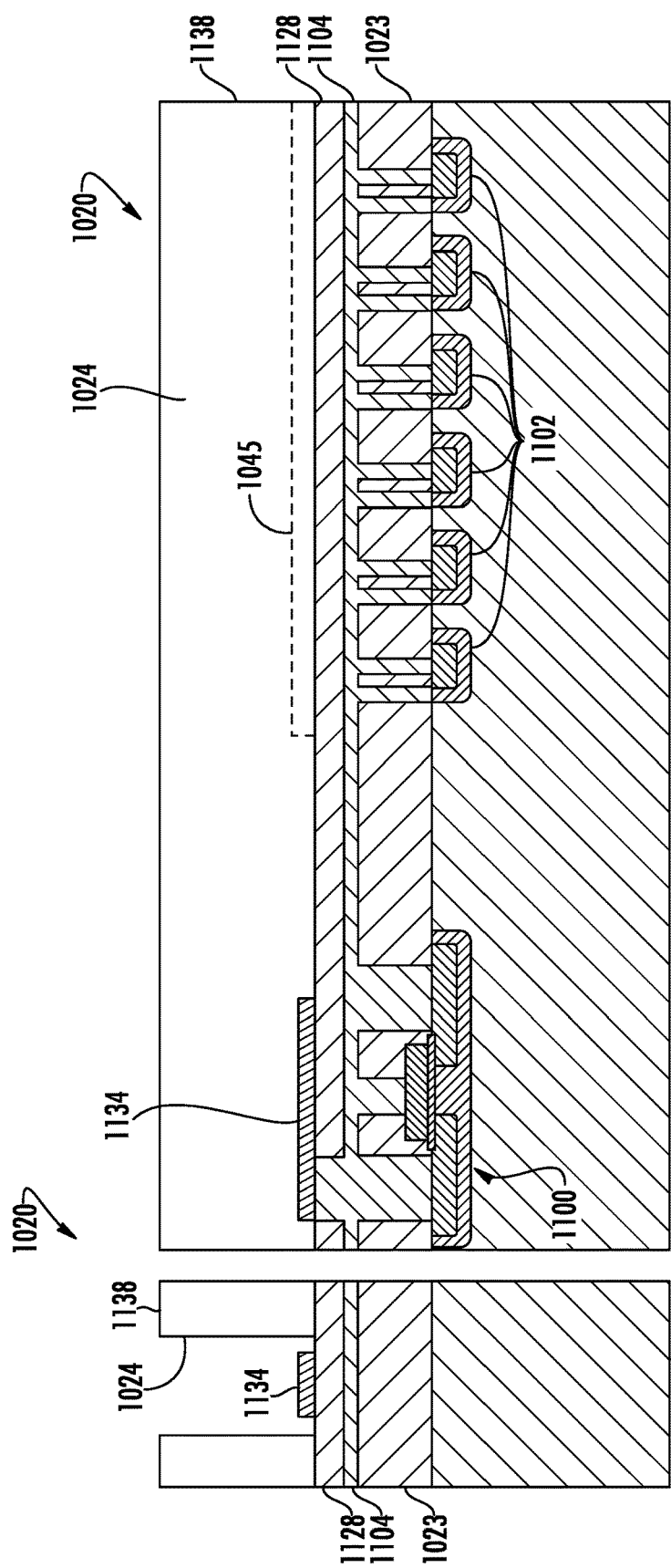

MICROFLUIDIC OPTICAL FLUID SENSOR

BACKGROUND

Various devices are available for sensing fluid constituents. Such fluid constituent sensing devices are often large, expensive and contain multiple separate components that need to be connected to one another.

BRIEF DESCRIPTION OF THE DRAWINGS

FIGS. 11-18 are sectional views schematically illustrating forming of another example microfluidic optical fluid sensor.

DETAILED DESCRIPTION OF EXAMPLES

Figure 1:
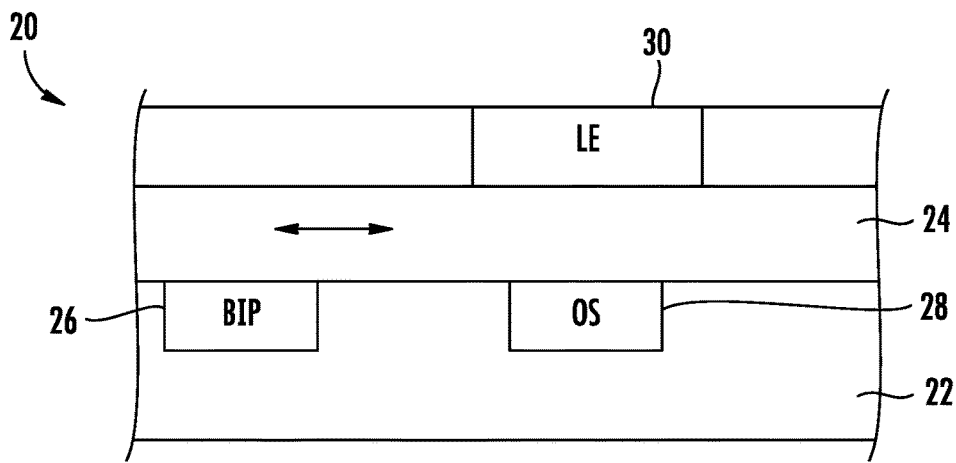
FIG. 1 is a schematic diagram of an example microfluidic optical fluid sensor.

FIG. 1 is a sectional view illustrating an example microfluidic optical fluid sensor 20. As will be described hereafter, fluid sensor 20 facilitates the sensing of fluid and fluid constituents on a single microfluidic chip or substrate. Sensor 20 may comprise substrate 22, microfluidic channel 24, bubble jet inertial pump 26, optical sensor 28 and light emitter 30.

Substrate 22 comprises a base or platform upon which the remaining components and associated electronics of sensor 20 are supported. In one implementation, substrate 22 comprises silicon. In other implementations, substrate 22 may comprise other materials. In one implementation, substrate 22 is provided as part of a wafer which is die cut into individual chips.

Microfluidic channel 24 comprises a conduit or a passage formed upon or within substrate 22 through which fluid or liquid being sensed and analyzed is directed. Microfluidic channel 24 has a width and height, each of which is in the sub-millimeter scale. In one implementation, microfluidic channel 24 has a width and height, each having a dimension of between 5 and 200 µm and nominally between 5 and 50 µm. Although illustrated as being linear, microfluidic channel 24 may have a curved, serpentine, branched or other shape.

Bubble jet inertial pump 26 may comprise a pump formed upon substrate 22 that produces an initially expanding bubble to move or drive adjacent fluid away from the bubble. One example of a bubble jet pump comprises a micro-heater, such as a thermal inkjet (TIJ) pump. A TIJ pump may utilize at least one electrical resistor through which electric current is passed. The heat produced by the at least one resistor as electric current passes through the at least one resistor may vaporize fluid that is proximate to the resistors to create a bubble. As this bubble is initially created and expands, the bubble may initially drive adjacent fluid away from the bubble. Bubble jet inertial pump 26 may be located along channel 24 proximate to a reservoir and distant to a different reservoir or fluid interaction component. In other words, the inertial pump is spaced from the reservoir by a distance less than one half of the length of the total fluid path between the reservoir and the other reservoir or fluid interaction component. Inertial pump may utilize inertia and momentum within a channel that is relatively narrow compared to the two reservoirs it connects to produce fluid flow. For purposes of this disclosure, the term "inertial pump" refers to a pumping device that initially drives fluid in both directions within a channel that is relatively narrow to the reservoirs it connects, but wherein the pumping device is asymmetrically positioned between the reservoirs such that the end result is fluid being driven in a direction towards the most distant of the two reservoirs.

Optical sensor 28 may comprise a device that outputs different logical signals in response to or based upon impingement of optical sensor 22 by electromagnetic radiation such as light. Optical sensor may be formed upon substrate 22 and be located so as to be impinged by light from light emitter 30 after such light emitter 30 has been directed or transmitted through and across microfluidic channel 24 and any fluid contained within microfluidic channel 24 in the path of the light. In one implementation, optical sensor 28 is located directly opposite to light emitter 30. In yet another implementation, optical sensor 28 received light or is impinged by light that has been directed across microfluidic channel 24 and that has been further propagated along a light pipe or waveguide. In one implementation, optical sensor 28 comprises a photoactive sensor, such as a charge coupled device, an example of which is a photodiode. In one implementation, optical sensor 28 may comprise a row or a two-dimensional array of individual optical sensing elements.

Light emitter 30 may comprise a device formed upon or within substrate that directs electromagnetic radiation, such as light, across microfluidic channel 24 and ultimately to optical sensor 28. As noted above, in one implementation, light emitter 30 transmits light directly to optical sensor 28 located directly across microfluidic channel 24. In another implementation, light emitter 30 transmits light across microfluidic channel 24 and to optical sensor 28 through a light pipe or waveguide. In one implementation, light emitter 30 emits or transmits a range of frequencies and/or wavelengths of light. In one implementation light emitter 30 comprises a light generating device, such as a light emitting diode. In another implementation, light emitter 30 comprises an opening or a transparent window through which light, from an external source not necessarily supported by substrate 22, provides light which is directed by light emitter 30 across microfluidic channel 24 and ultimately to optical sensor 28.

In operation, liquid or fluid from a fluid reservoir or other fluid source may be made available to and occupy microfluidic channel 24. To move the liquid or fluid through microfluidic channel 24 and across both regions within channel 24 through which light from light emitter 30 passes, bubble jet inertial pump 26 is actuated. Upon being actuated, bubble jet inertial pump 26, comprising a thermal inkjet resister, may need to a temperature sufficient us to vaporize portions of the fluid within channel 24 to greater vapor bubble which pushes fluid along microfluidic channel 24. As the fluid is being pushed and driven through microfluidic channel 24 through the light provided by light emitter 30, the light provided by light emitter 30 may interact differently with different constituents in the fluid. After interacting with the constituents within the fluid, the light may be further transmitted to optical sensor 28 which outputs electrical signals that vary in response to differing characteristics of the received light. Such varying electrical signals are transmitted to electronics, such as a processor, that analyzes the electrical signals to identify characteristics of the fluid, such as particular constituents, constituent counts and constituent sizes.

Figure 2:
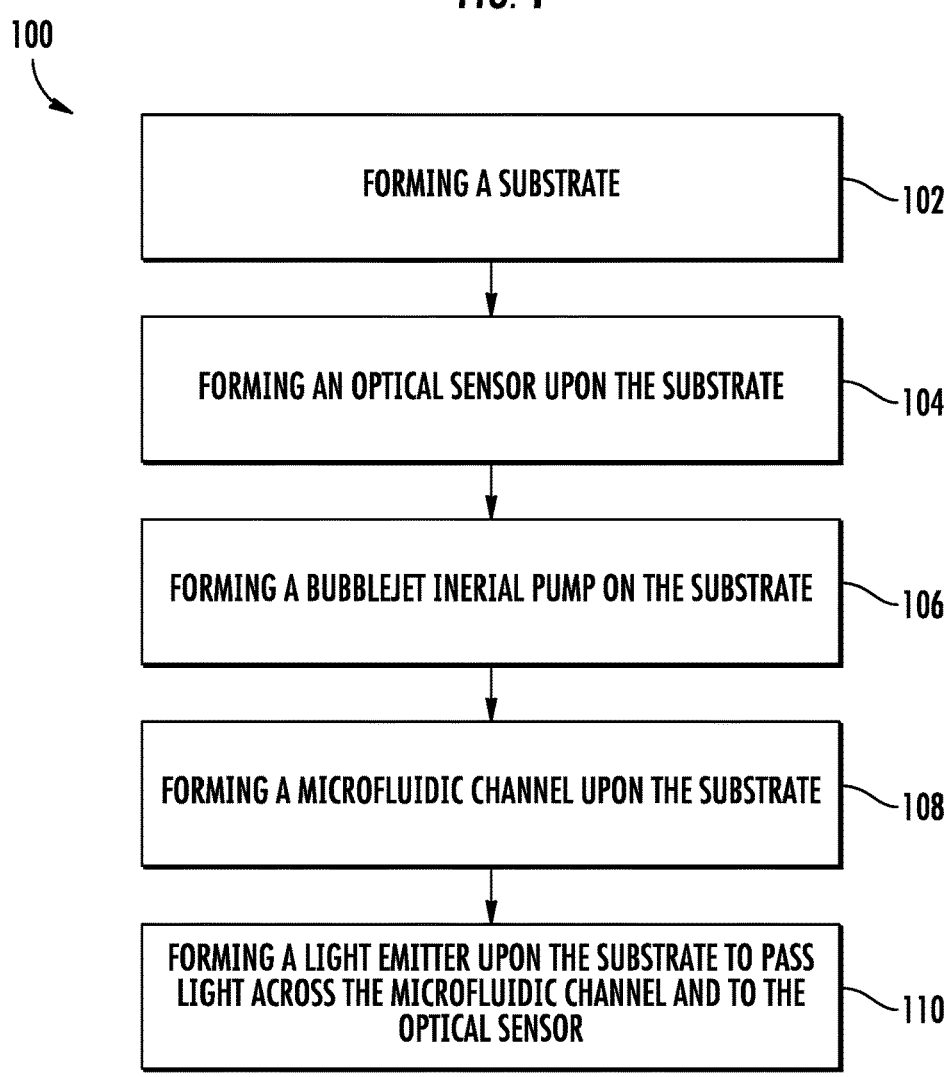
FIG. 2 is a flow diagram of an example method for forming a microfluidic optical fluid sensor.

FIG. 2 is a flow diagram of an example method 100 for forming microfluidic optical fluid sensor 20. As indicated by block 102, substrate 22 is formed. As indicated by block 104, optical sensor 28 is formed upon substrate 22. In one implementation, optical sensor 28 comprises a photoactive sensor, such as a charge coupled device, an example of which is a photodiode. In one implementation, optical sensor 28 may comprise a row or a two-dimensional array of individual optical sensing elements.

As indicated by block 106, bubble jet inertial pump 26 is formed upon substrate 104. Bubble jet inertial pump 26 is formed so pump liquid or fluid within microfluidic channel 24 upon being actuated. In one implementation, bubble jet inertial pump 26 comprises a thermal inkjet resister. In one implementation, bubble inkjet pump 26 comprises a transistor, formed upon substrate 22, such as a power field effect transistor, to facilitate selective actuation of the thermal inkjet resister of bubble jet inertial pump 26.

In one implementation, bubble jet inertial pump 26 is formed through semiconductor fabrication processes such that both project inertial pump 26 and optical sensor 28 are concurrently fabricated are formed during a single overall semiconductor fabrication process. For example, such semiconductor fabrication process may comprise both the formation of a field effect transistor, the thermal inkjet resister and components of the photodiodes or other charge coupled devices through the selective deposition and removal of materials upon a single substrate such as substrate 22. In one implementation, the optical sensor 28 is formed along with the complementary metal-oxide semiconductor (CMOS) electronics (silicon with doped regions, plus metal/dielectric interconnect layers) forming the transistor used to drive the heater resister of the bubble jet inertial pump. The thermal jet inkjet resister which is driven by the transistor is subsequently formed. As a result, costs and complexities associated with the fabrication and manufacture of sensor 22 may be reduced.

As indicated by block 108, microfluidic channel 24 is formed upon substrate 22. Unless otherwise specifically noted, the phrase "upon", when referring to a substrate, such as substrate 22, encompasses on top of, within or as part of substrate. In one implementation, microfluidic channel 24 is formed by selective chemical etching or other material removal processes. As noted above, microfluidic channel 24 may have various shapes and extends along various paths.

Because optical sensor 28 and bubble jet inertial pump 26 are both supported by substrate 22, upon substrate 22, liquid or fluid may pump through microfluidic channel 24 without the chip or other device providing microfluidic channel 24 being connected to a separate or independent pumping device. In other words, both pumping and sensing are integrated into a single substrate and possibly a single chip. For purposes of this disclosure, the term "integrated" with respect to a chip, substrate or microfluidic channel means that a device or component is integral with the chip or substrate or that the device or component is built into or as part of the chip or substrate in that at least one structures of the device or component are formed or fabricated upon the chip or substrate such that they cannot be readily separated without cutting or severing portions of the chip or substrate.

Because the pumping fluid in sensor 20 is provided by a bubble jet inertial pump, the dimensioning of microfluidic channels 24 may be smaller, facilitating a more compact substrate and a more compact sensor. The smaller size facilitates the provision of both a pump and an optical sensor on a single chip. Because pumping of fluid for sensor 20 is provided by a bubble jet inertial pump 26, the spacing between adjacent or multiple channels, or different portions of a channel may be reduced; further facilitating a more compact sensor 20.

As indicated by block 110, light emitter 30 is formed upon substrate 22 so as to pass light across the microfluidic channel and to the optical sensor 28. The passing or transmission of light across microfluidic channel to optical sensor 28 may be direct or may be indirect through light pipes or waveguides. In one implementation, light emitter 30 comprises a light generating device. In another implementation, light emitter 30 comprises an aperture or a transparent window through which light from a light generating device, whether upon substrate 22 or external to substrate 22, passes.

Figure 3:
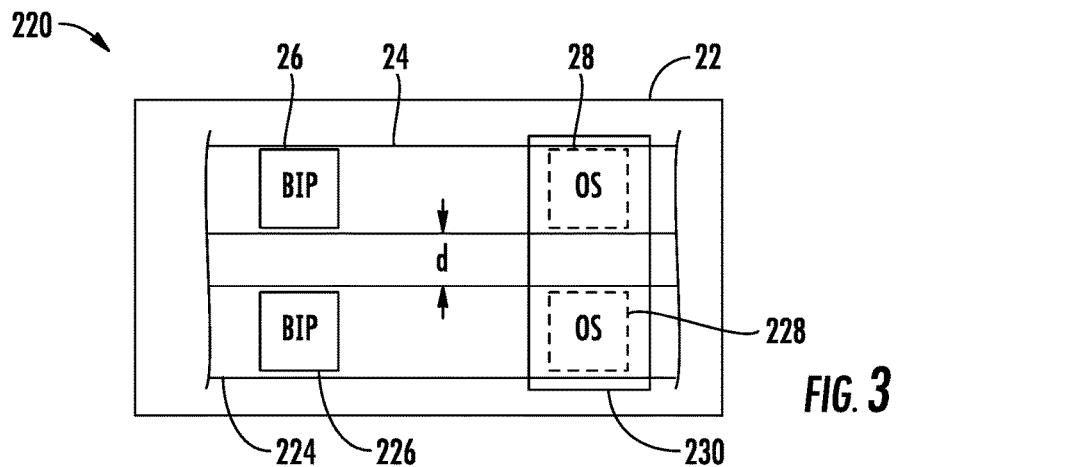
FIG. 3 is a top view schematically illustrating another example microfluidic optical fluid sensor.

FIG. 3 is a top view schematically illustrating microfluidic optical fluid sensor 220, an example of microfluidic optical fluid sensor 20. Microfluidic sensor 220 comprises substrate 22, microfluidic channel 24, bubble jet inertial pump 26, and optical sensor 28, each of which is described above with respect to system 20. Microfluidic sensor 220 further comprises microfluidic channel 224, bubble jet inertial pump 226, optical sensor 228 and light emitter 230. Microfluidic channel 224 is formed upon substrate 22 and is similar to microfluidic channel 24. In one implementation, microfluidic channel 224 and microfluidic channel 24 have adjacent sides that are spaced from one another by a distance d less than or equal to 42 µm and nominally less and 20 µm. In some implementations, such adjacent sides are spaced from one another by a distance of less than or equal to 5 µm. As noted above, the compact nature of bubble jet inertial pumps 26, 226 may facilitate forming microfluidic channels 24, 224 with reduced dimensions and into close proximity to one another. As a result, sensor 220 is more compact and/or may comprise a greater number of microfluidic channels, pumps 26, 226 and optical sensors 28, 228.

Bubble jet inertial pump 226 is similar to bubble jet inertial pump 26, except that bubble jet inertial pump 226 is formed and located so as to selectively pump fluid within microfluidic channel 224. Optical sensor 228 is similar to optical sensor 28, except that optical sensor 228 is formed upon and supported by substrate 22 so as to receive light that is passed through or across microfluidic channel 224. Although optical sensors 28 and 228 are illustrated as being directly opposite to or directly above/below microfluidic channels 24 and 224, respectively, in other implementations, optical sensors 28, 228 may be located along sides of channels 24, 224 or may be located at locations off-center spaced from channel 24, 224; wherein light that is passed through or across channels 24, 224 is further transmitted by light pipes or waveguides to the offset optical sensors 28, 228.

Light emitter 230 is similar to light emitter 30, except that light emitter 230 directs light across both of microfluidic channels 24, 224. In one implementation, light emitter 230 spans across both of microfluidic channels 24, 224. In another implementation, light emitter 230 directs light to waveguides or multiple waveguides that direct light across both of microfluidic channels 24, 224. Because the use of bubble jet inertial pumps 26, 226 may facilitate the forming and locating of channels 24, 224 into close proximity to one another, a single light emitter 230 may be employed for both channels.

Figure 4:
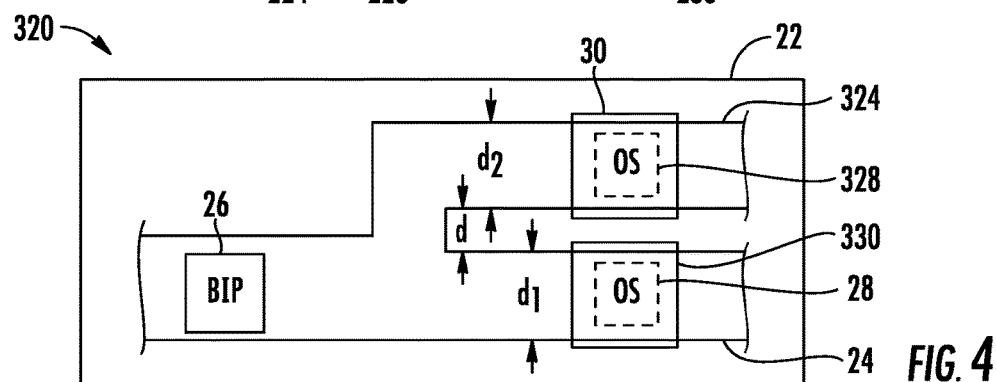
FIG. 4 is a top view schematically illustrating another example microfluidic optical fluid sensor.

FIG. 4 is a top view schematically illustrating microfluidic optical fluid sensor 320, another implementation of sensor 20. Microfluidic optical fluid sensor 320 comprises substrate 22, microfluidic channel 24, bubble jet inertial pump 26, optical sensor 28 and light emitter 30, each of which is described above with respect to sensor 20. Microfluidic optical fluid sensor 320 additionally comprises microfluidic channel 324, optical sensor 328 and light emitter 330.

Microfluidic channel 324 may comprise a conduit or passage formed upon or within substrate 22 through which fluid or liquid being sensed and analyzed is directed. Microfluidic channel 24 has a width and height, each of which is in the sub-millimeter scale. In one implementation, microfluidic channel 24 has a width and height, each having a dimension of between 5 and 200 µm and nominally between 5 and 50 µm. Although illustrated as being linear, microfluidic channel 24 may have a curved, serpentine, branched or other shape.

In the example illustrated, microfluidic channel 324 stems or branches off of microfluidic channel 24. Microfluidic channel 324 and microfluidic channel 24 have adjacent sides from one another by a distance d less than or equal to 42 µm, nominally less than 20 µm. In some implementations, distance d is less than or equal to 5 µm. In the example illustrated, microfluidic channel 24 has a dimension (width or height) d1 while microfluidic channel 324 has a corresponding dimension (width or height) d2 that is different than dimension d1. In the example illustrated, dimension d2 of channel 324 is less than dimension d1 of channel 24. The difference between dimensions d1 and d2 facilitates separation of the fluid flowing through channels. In one implementation, the differences between the dimensions d1 and d2 serves as a constituent size filter, wherein the smaller dimension d2 selectively inhibits the flow of particles, cells or other constituents which are too large (larger than d2) into channel 324. As a result, optical sensors 28, 328 and/or light emitters 30, 330 may be selected or customize based upon the constituents expected to flow through the differently sized channels 24, 324.

Optical sensor 328 is similar to optical sensor 28 except that while optical sensor 28 has properties for sensing a first type of constituents or a first group of constituents expected to flow through channel 24, optical sensor 328 is specifically customized or has specific sensing characteristics such as resolution or the like, adapted for or suited for sensing a second type of constituents or a second group of constituents, different than the first type constituents are first group of constituents, expected to flow through the differently dimensioned channel 324. In other implementations, optical sensors 328 and 28 are substantially identical.

Light emitter 330 is similar to optical sensor 30 except that while light emitter 30 has light emission properties to facilitate the sensing a first type of constituents or a first group of constituents expected to flow through channel 24 or to be more suitable for use with optical sensor 28, light emitter 330 is specifically customized or has specific light output characteristics such as wavelength, frequency, rate or the like, adapted for or suited to be more suitable for use with optical sensors 328 or to facilitate sensing a second type of constituents or a second group of constituents, different than the first type constituents or first group of constituents, expected to flow through the differently dimensioned channel 324. In other implementations, light emitters 30, 330 are substantially identical.

Figure 5:
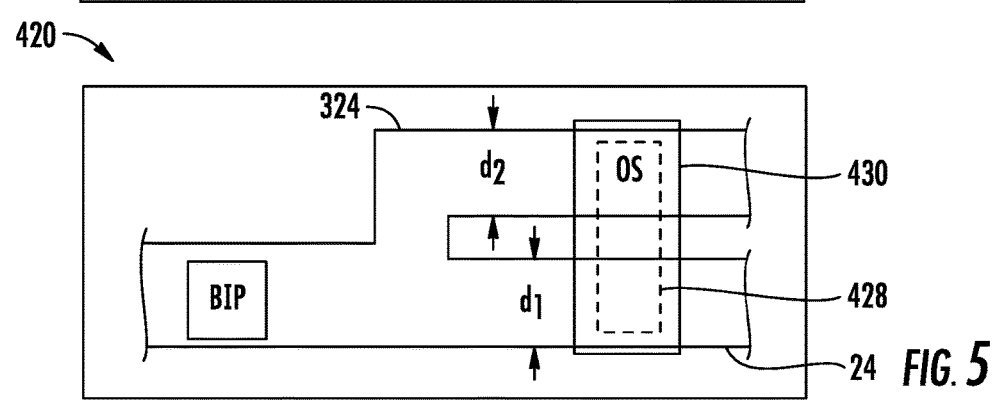
FIG. 5 is a top view schematically illustrating another example microfluidic optical fluid sensor.

FIG. 5 is a top view schematically illustrating microfluidic optical fluid sensor 420, another example of microfluidic optical fluid sensor 20. Microfluidic optical fluid sensor 420 is similar to sensor 320 except that sensor 420 shares a single optical sensor 28 and a single light emitter 430 amongst multiple microfluidic channels, channels 24 and 324. The close spacing between channels 24 and 324 facilitate sensor sharing. As a result, sensor 420 may be more compact, less complex and less expensive while offering fluid sensing along multiple channels.

Figure 6:
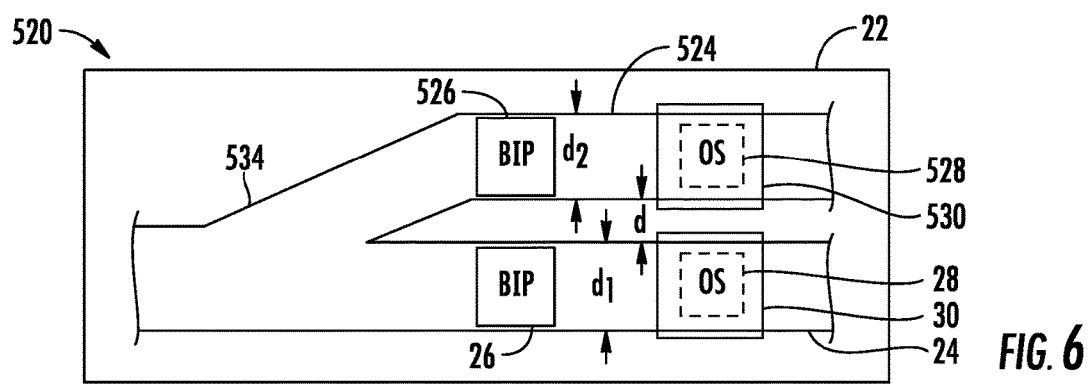
FIG. 6 is a top view schematically illustrating another example microfluidic optical fluid sensor.

FIG. 6 is a top view schematically illustrating microfluidic optical fluid sensor 520, another example of microfluidic optical fluid sensor 20. Microfluidic optical fluid sensor 520 comprises a substrate 22, microfluidic channel 24, bubble jet inertial pump 26, optical sensor 28 and light emitter 30 each of which are described above. Sensor 520 additionally comprises microfluidic channel 524, bubble jet inertial pump 526, optical sensor 528 and light emitter 530.

Microfluidic channel 524 stems from her branches off of microfluidic channel 24 a union or junction point 534. In the example illustrated, channels 24 and 524 are similar to channels 24 and 324 described above in that channels 24 and 524 have different dimensions d1 and d2. Channels 24, 524 are further closely spaced, having adjacent sides separated from one another by a distance d of less than or equal to 42 µm and nominally less than 20 µm. In some implementations, the distance D is less than or equal to 5 µm.

Similar to channels 24 and 324 of sensor 320, channels 24 and 524 of sensor 520 are each associated with different optical sensors and/or different light emitters that have different sensing characteristics or capabilities dependent upon the different types of particles, cells are constituents expected to flow within the respective channels 24, 524. While optical sensor 28 has properties for sensing a first type of constituents or a first group of constituents expected to flow through channel 24, optical sensor 528 is specifically customized or has specific sensing characteristics such as resolution or the like, adapted for or suited for sensing a second type of constituents or a second group of constituents, different than the first type constituents are first group of constituents, expected to flow through the differently dimensioned channel 524. In other implementations, optical sensors 528 and 28 are substantially identical, or identical. While light emitter 30 has light emission properties to facilitate the sensing a first type of constituents (such as cells, particles or the like) or a first group of constituents expected to flow through channel 24 or to be more suitable for use with optical sensor 28, light emitter 530 is specifically customized or has specific light output characteristics such as wavelength, frequency, rate or the like, adapted for or suited to be more suitable for use with optical sensors 528 or to facilitate sensing a second type of constituents or a second group of constituents, different than the first type constituents or first group of constituents, expected to flow through the differently dimensioned channel 524. In other implementations, light emitters 30, 530 are substantially identical, or identical.

Bubble jet inertial pump 526 is similar to bubble jet inertial pump 26 except that bubble jet inertial pump 526 is supported by and upon substrate 22 to selectively pump fluid through channel 524. In the example illustrated, bubble jet inertial pump 526 is located adjacent to channel 524 while bubble jet inertial pump 26 is located adjacent to that portion of channel 524 downstream of junction 534, that portion of channel 524 which runs alongside channel 524. In one implementation, bubble jet inertial pumps 26 and 526 have similar pumping characteristics. In another implementation, bubble jet inertial pumps 26 and 526 each possess pumping characteristics different form one another, each pump having a size or pumping characteristics and capabilities customized or most suited for the different sizes or dimensions of their respective channels 24, 524, most suited for the particular optical sensors 28, 528 and/or light emitters 30, 530 associated with their respective channels 24, 524 and/or most suited for the different types of fluid or fluid constituents expected or anticipated to flow through the respective channels 24, 524 due to the different dimensioning or relationship of channels 24, 524.

In the example illustrated, bubble jet inkjet pumps 26, 526 are selectively actuatable independent of one another to control or vary the movement of fluid through the respective channels 24, 524. In one implementation, pumps 26, 526 are selectively actuatable to pump fluid or move fluid through channels 24 and 524 at different non-zero rates. In one implementation, pumps 26 and 526 are selectively actuatable independent of one another such that pumps 26 and 526 serve or function as microfluidic valves, selectively closing off one or both of channels 24, 524 or impeding or reducing the flow of fluid through the respective channels 24, 524. Because pumps 26, 526 comprise bubble jet inertial pumps, which are integrated into substrate 22 and which are relatively compact in size, pumps 26, 526 may be situated in each of these side-by-side portions of channels 24, 524 to provide the aforementioned functions without reducing the close spacing of channels 24, 524 or the compact nature of sensor 520.

Figure 7:
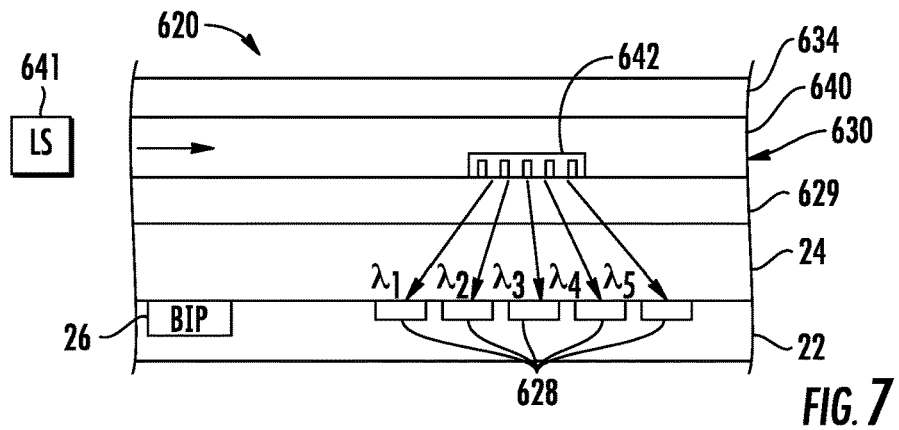
FIG. 7 is a sectional view schematically illustrating another example microfluidic optical fluid sensor.

FIG. 7 is a sectional view schematically illustrating microfluidic optical fluid sensor 620. Microfluidic optical sensor 620 comprises substrate 22, microfluidic channel 24 and bubble jet inertial pump 26, each of which is described above with respect to system 20. Sensor 620 additionally comprises optical sensors 628, transparent spacer layer 629 and light emitter 630. Optical sensors 628 comprise an array of optical sensors. Each sensor is similar to optical sensor 28 described above. In the example illustrated, optical sensors 628 and the electrical interconnects and transistor of bubble jet inertial pump 26 are integrated upon substrate 22. In one implementation, optical sensors 628 and portions of bubble jet inertial pump 26 are formed during a single CMOS fabrication process.

Transparent spacer layer 629 comprises a layer of transparent material spacing waveguide 630 from optical sensors 628.

Light emitter 630 transmits light across microfluidic channel 24 towards optical sensors 628. Light emitter 630 comprises waveguide 640 which is covered a coated with an overlying opaque, light blocking cladding layer 634. Waveguide 640 comprises grating 642. Waveguide 640 transmits light from a light source 641 to grating 642. Grating 642 concurrently directs different wavelengths of light across microfluidic channel 24. The different wavelengths of light differently diffract or bend at different angles when passing through the fluid within microfluidic channel 24. Due to the spacing provided by transparent spacer layer 629, the different wavelengths of light, such as different colors of light, impinge different individual optical sensors 628. As a result, system 620 utilizes light from a single light source, light source 641, to detect characteristics of the fluid within microfluidic channel 24 using multiple different wavelengths of light.

Figure 8:
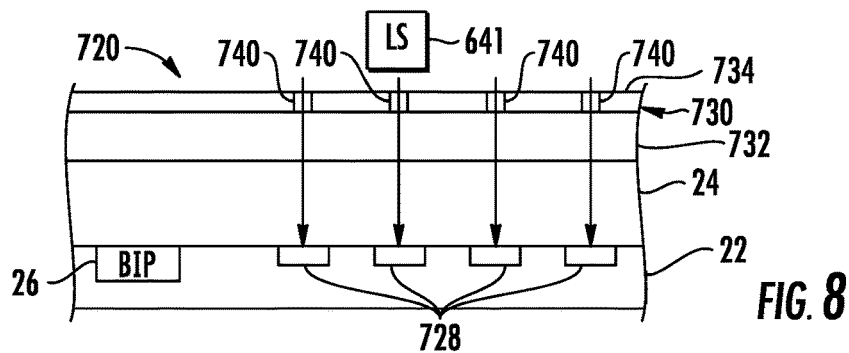
FIG. 8 is a sectional view schematically illustrating another example microfluidic optical fluid sensor.

FIG. 8 is a sectional view schematically illustrating microfluidic optical fluid sensor 720. Microfluidic optical sensor 720 comprises substrate 22, microfluidic channel 24 and bubble jet inertial pump 26, each of which is described above with respect to system 20. Sensor 720 additionally comprises optical sensors 728 and light emitter 730.

Optical sensors 728 comprise an array of optical sensors. Each optical sensor 728 is similar to optical sensor 28 described above. In the example illustrated, optical sensors 728 and the electrical interconnects and transistor of bubble jet inertial pump 26 are integrated upon substrate 22. In one implementation, optical sensors 728 and portions of bubble jet inertial pump 26 are formed during a single CMOS fabrication process.

Light emitter 730 transmits light across microfluidic channel 24 towards optical sensors 728. Light emitter 630 comprises transparent support layer 732 and opaque or light blocking layer 734. Support layer 732 forms or defines microfluidic channel 24 and supports layer 734. Layer 734 comprises a layer light blocking material, such as a metal or other coating. Layer 734 comprises multiple apertures 740 corresponding to and substantially aligned with optical sensors 728. Apertures 740 are located such that light from light source 641 passes through each of apertures 742 across microfluidic channel 24 to a corresponding one of optical sensors 728. Each of apertures 740 has a light transmitting area or a cross-sectional area that is smaller than the light receiving area or cross-sectional area of the corresponding optical sensor 728. Sensor 720 provides enhanced spatial resolution for sensing with the array of optical sensors 728.

Figure 9:
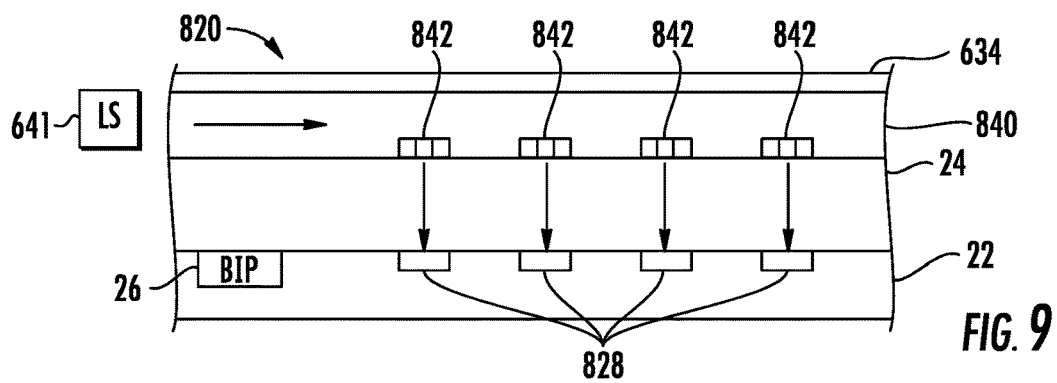
FIG. 9 is a sectional view schematically illustrating another example microfluidic optical fluid sensor.

FIG. 9 is a sectional view schematically illustrating microfluidic optical fluid sensor 820. Microfluidic optical sensor 820 comprises substrate 22, microfluidic channel 24 and bubble jet inertial pump 26, each of which is described above with respect to system 20. Sensor 820 additionally comprises optical sensors 828 and light emitter 830. Optical sensors 828 comprise an array of optical sensors. Each sensor is similar to optical sensor 28 described above. In the example illustrated, optical sensors 828 and the electrical interconnects and transistor of bubble jet inertial pump 26 are integrated upon substrate 22. In one implementation, optical sensors 828 and portions of bubble jet inertial pump 26 are formed during a single CMOS fabrication process.

Light emitter 830 transmits light across microfluidic channel 24 towards optical sensors 828. Light emitter 830 comprises waveguide 840. Waveguide 840 comprises multiple spaced gratings 842. Waveguide 840 transmits light from a light source 641 to gratings 842. Grating 842 concurrently direct different wavelengths of light across microfluidic channel 24. The different wavelengths of light impinge the different optical sensors 628, whereby these transmission of light across the fluid within microfluidic channel 24 at different wavelengths is detected. System 820 facilitates irregular spacing of optical sensors 828.

In one implementation, each of gratings 842 comprises a similar grating, wherein optical sensors 828 are appropriately offset relative to their associated grating so as to be impinged by a selected portion of the different wavelengths of light emitted from the associated grating 842. For example, in one implementation, one of optical sensors 828 may be positioned relative to its corresponding grating 842 so as to be impinged by a first wavelength of light from its corresponding grating while another of optical sensors 828 is differently offset relative to its corresponding grating 842 so as to be impinged by a different wavelengths of light from its corresponding grating 842. In such an implementation, a portion or fraction of the total wavelengths of light from each grating are sensed. In yet another implementation, the periods of each of gratings 842 vary such that each optical sensor 828 receives a particular preselected wavelength of light. In each of such implementations, different wavelengths of light passing through fluid within microfluidic channel 24 are concurrently sensed to facilitate analysis of the fluid within microfluidic channel 24.

Figure 10:
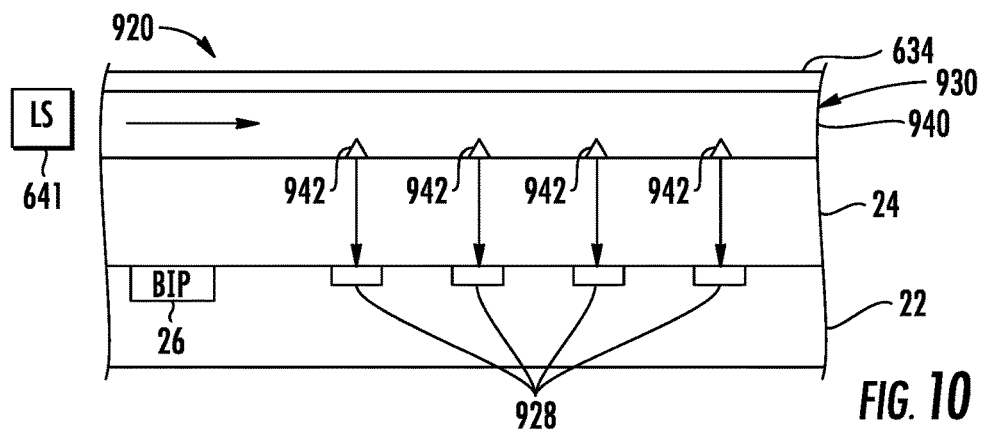
FIG. 10 is a sectional view schematically illustrating another example microfluidic optical fluid sensor.

FIG. 10 is a sectional view schematically illustrating microfluidic optical fluid sensor 920. Microfluidic optical sensor 920 comprises substrate 22, microfluidic channel 24 and bubble jet inertial pump 26, each of which is described above with respect to system 20. Sensor 920 additionally comprises optical sensors 928 and light emitter 630. Optical sensors 928 comprise an array of optical sensors. Each sensor is similar to optical sensor 28 described above. In the example illustrated, optical sensors 928 and the electrical interconnects and transistor of bubble jet inertial pump 26 are integrated upon substrate 22. In one implementation, optical sensors 928 and portions of bubble jet inertial pump 26 are formed during a single CMOS fabrication process.

Light emitter 930 transmits light across microfluidic channel 24 towards optical sensors 928. Light emitter 930 comprises waveguide 940 and. multiple spaced light scatterers 942. Waveguide 840 transmits light from a light source 641 to scatterers 942. Scatterers 942 concurrently direct the same light across microfluidic channel 24. In this way, a single light source and waveguide, with integrated scatterers, provide illumination in front of many optical sensors 928, such as photodiodes, placed at different locations along microfluidic fluidic channel 24, or along different microfluidic fluidic channels, such as channels 24 and 324 described above. As a result, sensor 920 may offer more efficient or more intense illumination than blanket illumination over an array of optical sensors.

Figure 11:
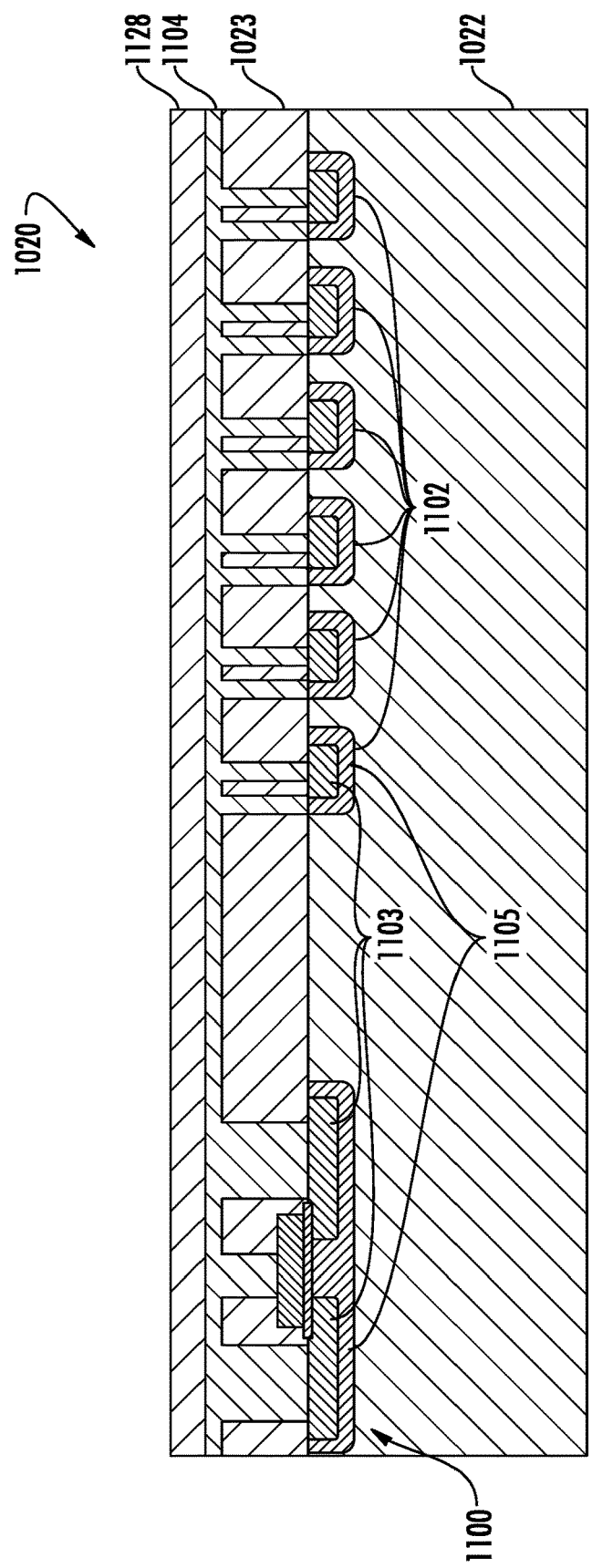
Figure 16:
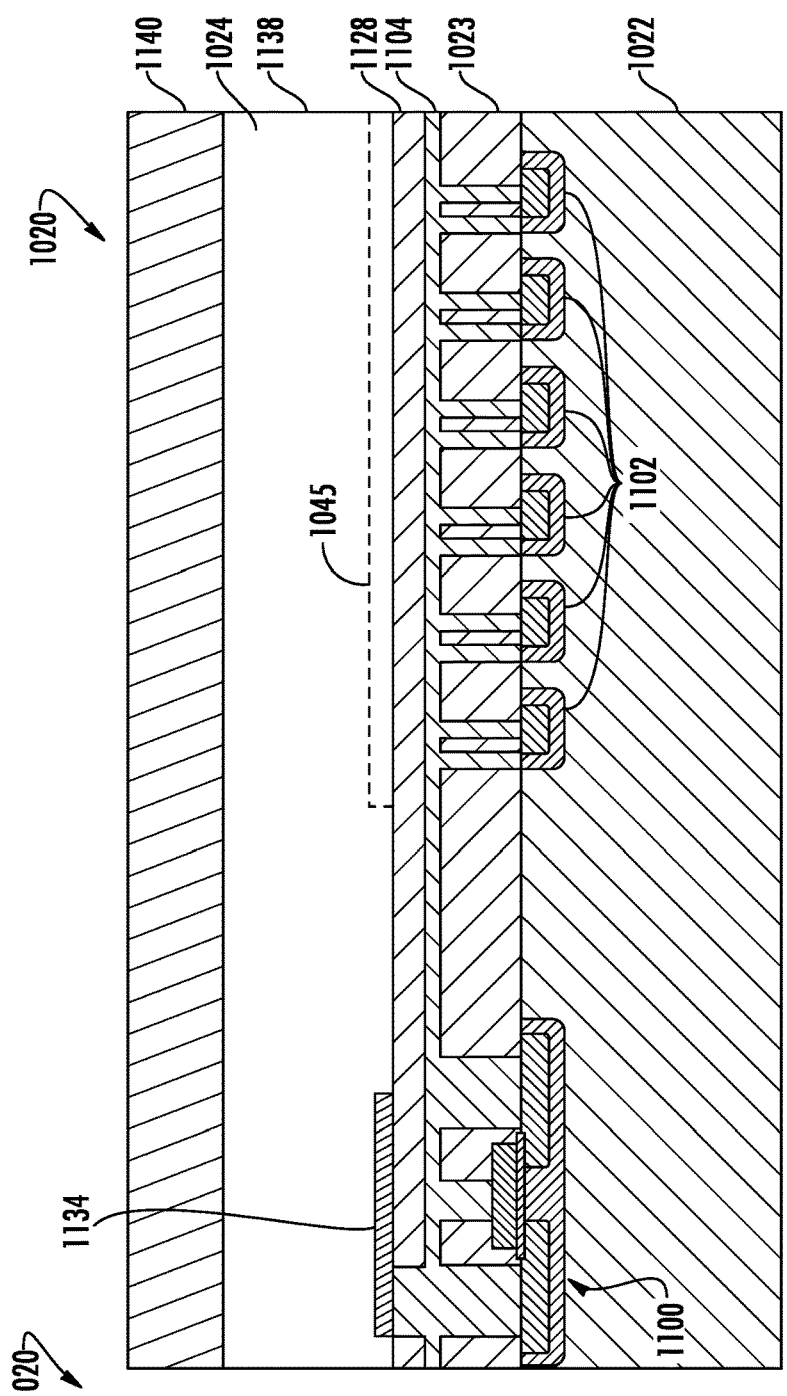
Figure 17:
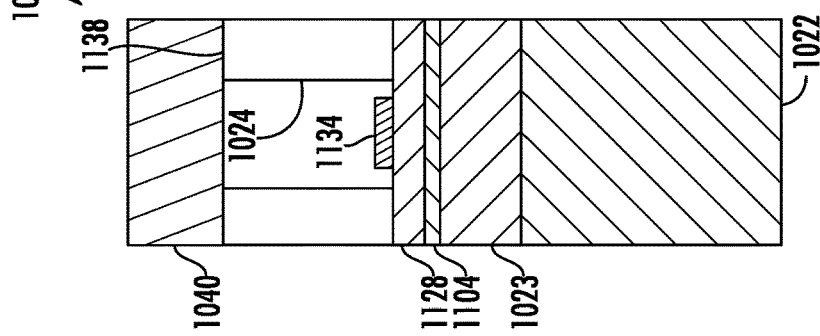

FIGS. 11-17 illustrate the formation process of an example microfluidic optical fluid sensor 1020 (shown completed in FIG. 17). As shown by FIG. 11, semiconductor fabrication processes are carried out with respect to a substrate 1022 to form a field effect transistor 1100 (comprising a source, a drain, a gate and a semiconductor channel) and an array of photodiodes 1102 upon substrate 1022. In the example illustrated, portions of the transistor 1100 and the photodiodes 1102 each includes concurrently formed p-type doping regions 1103 and n-type doping regions 1105. Metal/dielectric layers 1023 are formed or patterned upon substrate 1022 and comprise various electrical interconnects 1104 (schematically shown) for transistor 1100 and photodiodes 1102. In the example illustrated, complementary metal-oxide-semiconductor (CMOS) processes are employed to form such structures. In the example illustrated, substrate 1022 comprises a silicon substrate. In other implementations, other semiconductor processes may be employed and substrate 1022 may be formed from other materials.

Figure 12:
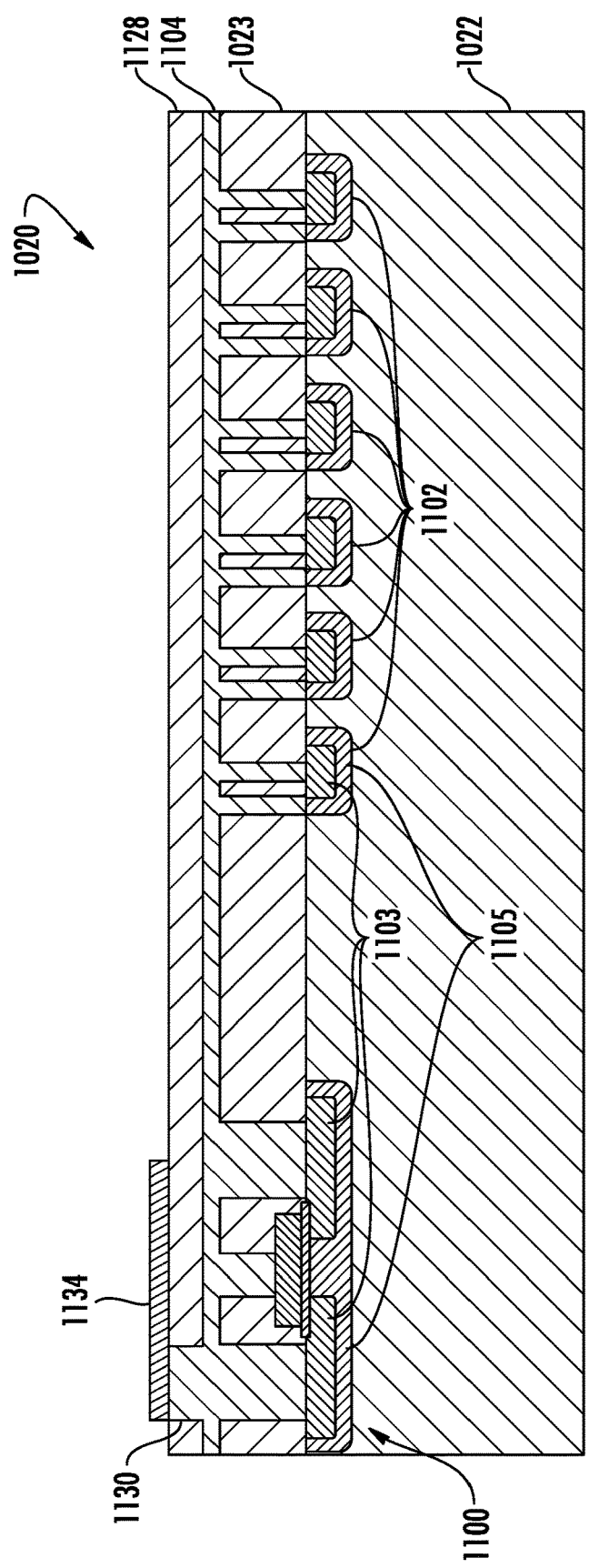
Figure 13:
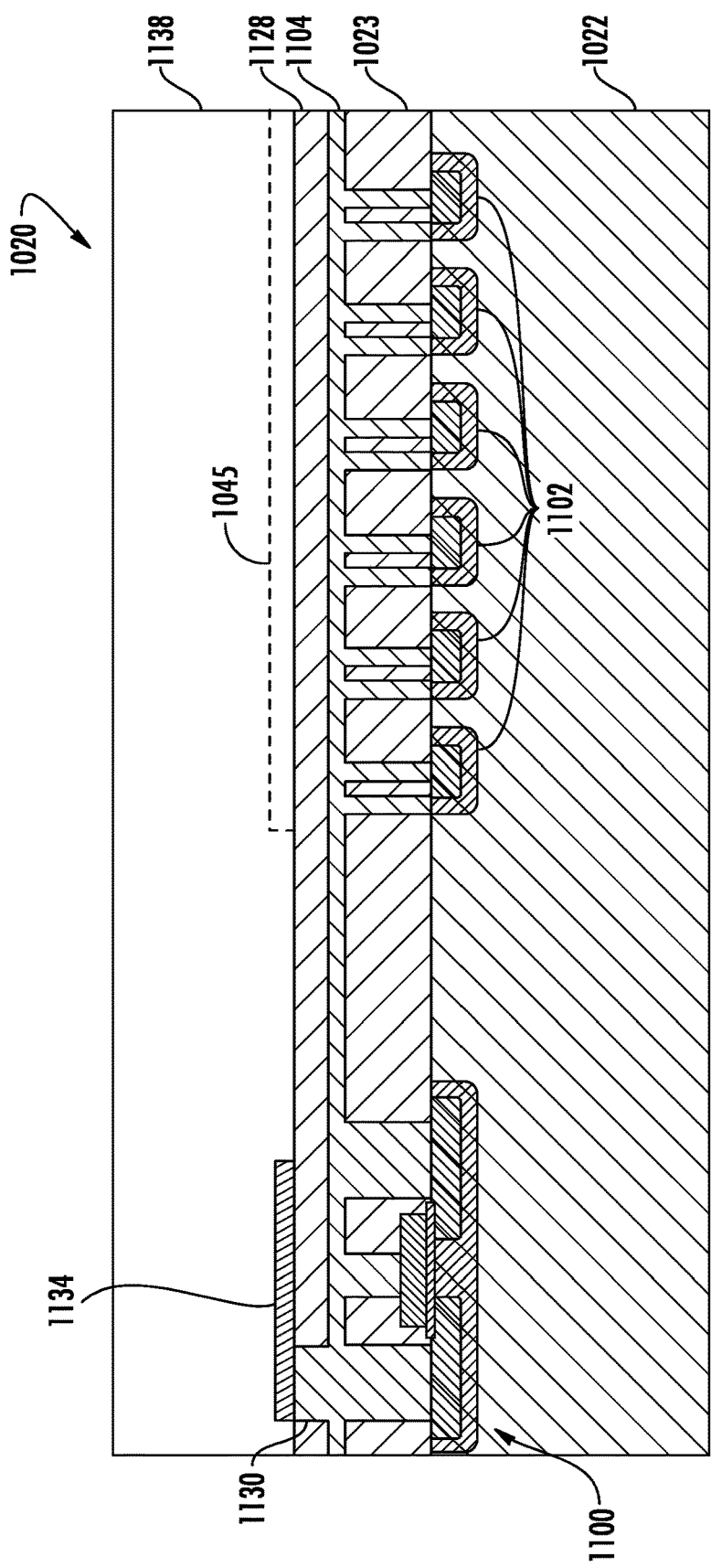

As illustrated by FIG. 12, the thermal inkjet resistor 1134 is formed upon dielectric layer 1128 and is electrically connected to transistor 1100 through via 1130. As illustrated by FIG. 13, a channel forming layer 1138 is formed upon layer 1128 and upon resistor 1134. In one implementation, layer 1138 comprises a layer of transparent photoresist material such as an epoxy-based negative photoresist such as SU-8 (Bisphenol A novolac epoxy that has been dissolved in organic solvent (such as gamma butylaractone GBL or cyclopentanone). As illustrated by FIGS. 14 and 15, layer 1138 is further exposed and developed to form microfluidic channel 1024. As illustrated by FIGS. 16 and 17, a transparent cover layer 1140 is formed or deposited on layer 1128 over are across microfluidic channel 1024. In some implementations, a lens may additionally be formed opposite to or over microfluidic channel 1024.

Figure 18:
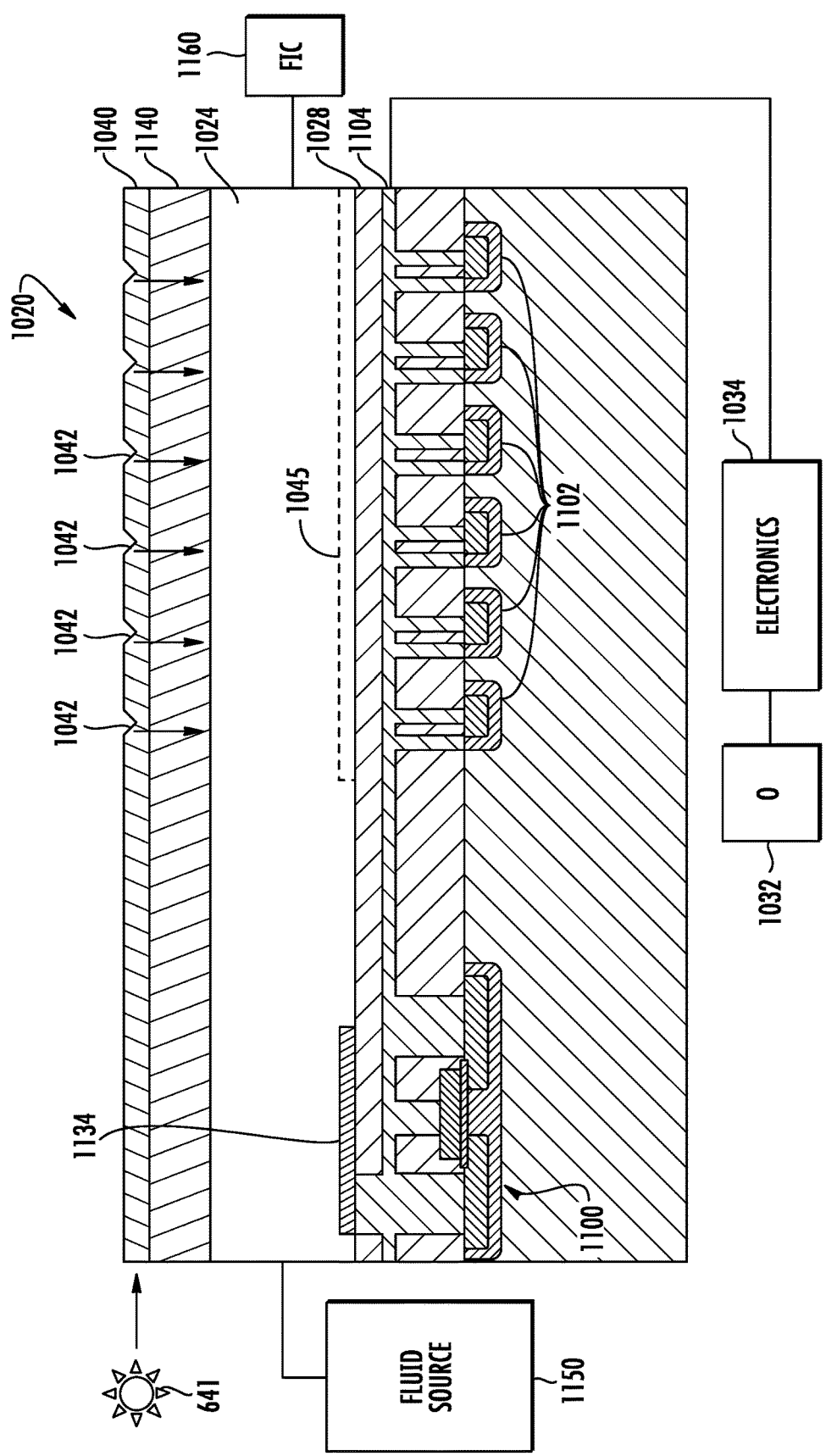

As illustrated by FIG. 18, a waveguide layer 1040, to serve as a light emitter for photodiodes 1102, is deposited or formed upon cover layer 1140. Portions of waveguide layer 1040 are removed to form light scatterers 1042. Light scatterers 1042 redirect light through cover layer 1140 and through channel 1024 to corresponding and aligned photodiodes 1102. In one implementation, the material for the waveguide layer 1040 comprises silicon nitride. In one implementation, the silicon nitride or other material forming waveguide layer 1040 is deposited using plasma enhanced chemical vapor deposition. In other implementations, the waveguide layer 1040 may be formed from other materials and may be formed in other fashions.

As illustrated by broken lines in FIG. 18, in one implementation, a layer of material which serves as an optical filter 1045 may be deposited upon layer 1028 such that light from scatters 1042, after passing through the fluid within microfluidic channel 1024, passes through the optical filter 1045 before reaching photodiodes 1102. Optical filter 1045 filters out particular wavelength of light to facilitate fluorescent signal detection, such as where cells, biomolecules, particles or other constituents in the fluid being analyzed have been tagged with optical or fluorescent markers which give off a specific signature at a particular wavelength or range of wavelengths. In other implementations, optical filter 1045 may be provided at other locations or upon other layers so as to filter light passing through microfluidic channel 1024. In still other implementations, optical filter 1045 may be omitted.

As further illustrated by FIG. 18, sensor 1020 is connected to or communicates with analysis electronics 1034. Output 1032 comprises a device by which the results of analysis of the liquid by electronic 1034 are presented and/or stored. In one implementation, output 1032 comprises a display screen or monitor. In one implementation, the display screen or monitor further serves as an input device, comprising a touch screen. In one implementation, output 1032 comprises a memory, wherein data from the sensing an analysis of the liquid that flows through microfluidic channel 1024 is stored. In one implementation, output 1032 is located external or independent of the chip providing the other components of sensor 1020, wherein output 1032 is connected to electronics 1034 in a wired or wireless fashion.

Electronics 1034 comprises a device that controls the operation of sensor 1020 and receives signals from photodiodes 1102 and utilizes such signals (either in a raw format or after such signals have been filtered, converted or processed by electronics 1034) to identify or determine characteristics of the fluid flowing through microfluidic channel 1024. For example, in one implementation, electronics 1034, following instructions contained in a non-transitory computer-readable medium or memory, analyzes signals received from photodiodes 1102 to identify a count or number of a particular constituent or cells in the liquid or fluids flowing within microfluidic channel 1024. In another implementation, electronics 1034 follows instructions contained in a non-transitory computer-readable medium to identify particular constituent of the fluid or characteristics of the constituents in the fluid flowing or otherwise within microfluidic channel 1024. The results of such analysis are transmitted to output 1032.

For purposes of this application, the term "processing unit" shall mean a presently developed or future developed processing unit comprising hardware that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other implementations, hard wired circuitry may be used in place of or in combination with software instructions to implement the functions described. For example, electronics 34 may be provided as part of at least one application-specific integrated circuits (ASICs). Unless otherwise specifically noted, the controller is not limited to any specific combination of hardware circuitry and software, nor to any particular source for the instructions executed by the processing unit.

In one implementation, the electronics comprises a memory storing a predetermined lookup table that correlates different electrical signals from photodiode 1102 to different fluid constituent counts and/or different fluid constituent characteristics. In such an implementation, the processing unit identifies fluid constituent counts or fluid constituent characteristics by comparing the electrical signals from photodiode 1102 to the different values in the lookup table.

In one implementation, fluid sensor 1020 is entirely contained or integrated upon substrate 1022 or the circuit chip containing microfluidic channel 1024. For example, in one implementation, electronics 1034 are each integrated as part of the chip or substrate 1022 in or on which microfluidic channel 1024 is provided. In yet other implementations, portions of fluid sensor 1020 are distributed among separate substrates or devices. For example, in one implementation, output 1032 and electronics 1034 are provided by a separate device that is electrically connected to electrical contacts or elliptical contact pads provided on the chip containing the remaining elements of sensor 1020.

In operation, electronics 1034 outputs control signals which are transmitted by selected interconnects 1104 to the transistor 1100 so as to activate bubble jet inertia pump 1026. As a result, fluid containing constituents is pumped are moved along microfluidic channel 1024. Light from light emitter 641 is transmitted to light scatters 1042 which redirect light to photodiodes 1102. Photodiodes 1102 transmit electrical signal to electronics 1034. Electronic 1034 analyzes the light, as represented by the electrical signals, to determine particular characteristics of the fluid being sensed. The results of the analysis are stored and/or presented on output 632.

In the example illustrated, microfluidic channel 1024 is connected to a fluid source 1150 so as to draw fluid from the fluid source 1150. In one implementation, fluid source 1150 comprises a reservoir. In another implementation, fluid source 1150 comprises a fluid loading port. In one implementation, fluid source 1150 supplies cells or biomolecules, such as cells or biomolecules that have been tagged with an optical (fluorescent) marker that provides a given signature at a given wavelength. Such markers facilitate the identification of different cells or biomolecules downstream by sensor 1020.

In the example illustrated, microfluidic channel 1024 is further connected to fluid interaction component 1160. Fluid interaction upon 1160 receives fluid pumped through microfluidic channel 1024 and further interacts with the fluid. In one implementation, fluid interaction component 1160 performs post processing such as cell sorting and counting. In another implementation, fluid interaction component 1160 mixes the fluid, separates and discharges different constituents of the fluid and/or adds additional fluids or analyte to the stream of fluid. In each of the various implementations described in FIGS. 1-10, the microfluidic channels of sensors 220, 320, 420, 520, 620, 720, 820, 920 may additionally be connected to fluid source 1150 and/or fluid interaction component 1160.

Although the present disclosure has been described with reference to example implementations, workers skilled in the art will recognize that changes may be made in form and detail without departing from the spirit and scope of the claimed subject matter. For example, although different example implementations may have been described as including at least one feature providing at least one benefit, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements.

What is claimed is:

1. A method comprising:
  forming a substrate;
  forming microfluidic channel upon the substrate;
  forming a bubble jet inertial pump upon the substrate to pump fluid through the microfluidic channel;
  forming an optical sensor upon the substrate to receive light passing through the microfluidic channel; and
  forming a light emitter on the substrate to pass light across the microfluidic channel into the optical sensor.

2. The method of claim 1 further comprising forming a second microfluidic channel upon the substrate; wherein the optical sensor is adjacent the second microfluidic channel to receive light emitted by the light emitter that has passed across the second microfluidic channel.

3. An apparatus comprising:
  a substrate;
  a microfluidic channel supported by the substrate;
  a bubble jet inertial pump integrated with the substrate and adjacent the microfluidic channel to selectively pump fluid through the microfluidic channel;
  an optical sensor integrated with the substrate adjacent and on a first side of the microfluidic channel; and
  a light emitter on a second side of the microfluidic channel to pass light across the microfluidic channel to the optical sensor.

4. The apparatus of claim 3 further comprising optical sensors along the microfluidic channel, wherein the light emitter comprises a waveguide along the microfluidic channel to direct light to each of the optical sensors.

5. The apparatus of claim 3 further comprising:
  a second microfluidic channel supported by the substrate.

6. The apparatus of claim 5, wherein the light emitter is to concurrently, pass light across the microfluidic channel and the second microfluidic channel.

7. The apparatus of claim 5, wherein the optical sensor is adjacent the second microfluidic channel to receive light emitted by the light emitter that has passed across the second microfluidic channel.

8. The apparatus of claim 5, wherein the second microfluidic channel branches off of the first microfluidic channel and wherein the apparatus further comprises:
    a second optical sensor supported by the substrate adjacent the second microfluidic channel; and
    a second bubble jet inertial pump supported by the substrate and adjacent the second channel to selectively pump fluid through the second microfluidic channel.

9. The apparatus of claim 5, wherein the light emitter concurrently directs light across the microfluidic channel and the second microfluidic channel.

10. The apparatus of claim 5, wherein adjacent sides of the first microfluidic channel and the second microfluidic channel are spaced from one another by less than or equal to 42 μm.

11. An apparatus comprising:
    a substrate;
    a first microfluidic channel supported by the substrate and having a width of less than or equal to 42 μm;
    a second microfluidic channel supported by the substrate and having a width of less than or equal to 42 μm, wherein adjacent sides of the first microfluidic channel and the second microfluidic channel are spaced by less than or equal to 42 μm;
    at least one bubble jet inertial pump integrated with the substrate and adjacent the first microfluidic channel and the second microfluidic channel to pump fluid through the first microfluidic channel and the second microfluidic channel;
    at least one optical sensor integrated with the substrate and on a first side of each of the first microfluidic channel and the second microfluidic channel; and
    at least one light emitter on a second side of each of the first microfluidic channel and the second microfluidic channel, the at least one light emitter to transmit light across the first microfluidic channel and the second microfluidic channel to the at least one optical sensor.

12. The apparatus of claim 11, wherein the second microfluidic channel branches off of the first microfluidic channel and wherein the at least one bubble jet inertial pump comprises:
    a first bubble jet inertial pump adjacent the first microfluidic channel to selectively pump fluid through the first microfluidic channel; and
    a second bubble jet inertial pump adjacent the first microfluidic channel to selectively pump fluid through the second microfluidic channel.

13. The apparatus of claim 11, wherein the first microfluidic channel has a first cross-sectional area and wherein the second microfluidic channel has a second cross-sectional area different than the first cross-sectional area.

14. The apparatus of claim 11, wherein the at least one optical sensor comprises a single optical sensor to be concurrently impinged by light transmitted across the first microfluidic channel and the second microfluidic channel.

15. The apparatus of claim 11, wherein the optical sensor is on a first side of the microfluidic channel and wherein the at least one bubble jet inertial pump is located on a second side of the microfluidic channel.

\* \* \* \* \*

UNITED STATES PATENT AND TRADEMARK OFFICE
CERTIFICATE OF CORRECTION

PATENT NO. : 10,365,226 B2
APPLICATION NO. : 15/546936
DATED : July 30, 2019
INVENTOR(S) : Alexander Govyadianov et al.

It is certified that error appears in the above-identified patent and that said Letters Patent is hereby corrected as shown below:

In the Claims

In Column 12, Line 40, Claim 2, delete "substrate;" and insert -- substrate, --, therefor.

In Column 12, Line 62, Claim 6, delete "concurrently," and insert -- concurrently --, therefor.

Signed and Sealed this
Twelfth Day of November, 2019

Andrei Iancu
*Director of the United States Patent and Trademark Office*